US006758671B2

(12) United States Patent
Brattesani

(10) Patent No.: US 6,758,671 B2
(45) Date of Patent: **\*Jul. 6, 2004**

(54) INFLATABLE DENTAL IMPRESSION TRAY AND MIXING TIP

(76) Inventor: Steven J. Brattesani, 3309 Fillmore St., San Francisco, CA (US) 94123

( * ) Notice: Subject to any disclaimer, the term of this patent is extended or adjusted under 35 U.S.C. 154(b) by 114 days.

This patent is subject to a terminal disclaimer.

(21) Appl. No.: 10/099,549

(22) Filed: Mar. 13, 2002

(65) Prior Publication Data

US 2002/0150860 A1 Oct. 17, 2002

Related U.S. Application Data

(63) Continuation of application No. 09/596,296, filed on Jun. 16, 2000, now Pat. No. 6,364,661.

(51) Int. Cl.$^7$ ................................................ A61C 9/00
(52) U.S. Cl. ..................................................... 433/37
(58) Field of Search ........................... 433/37, 36, 214, 433/80

(56) References Cited

U.S. PATENT DOCUMENTS

| | | | |
|---|---|---|---|
| 1,093,125 | A | 4/1914 | Guilford |
| 2,311,158 | A | 2/1943 | Conway et al. |
| 2,488,922 | A | 11/1949 | Mead |
| 4,573,916 | A | 3/1986 | Sturtzkopf |
| 4,583,916 | A | 4/1986 | Senghaas et al. |
| 5,665,066 | A | 9/1997 | Fischer |
| 5,752,826 | A | 5/1998 | Andreiko |
| 5,819,988 | A | 10/1998 | Sawhney et al. |
| 5,890,895 | A | 4/1999 | Tucker |

FOREIGN PATENT DOCUMENTS

| EP | 319639 | 7/1987 |
|---|---|---|
| FR | 2552658 | 10/1983 |

OTHER PUBLICATIONS

Dentsply Trubyte Bite Block & Edentulous Custom Tray, Dentsply International—Trubyte Division, 570 College Avenue, P.O. Box 872, York, PA 17405–0872 http://www.trubyte.com/triad.htm (3 pages)—Screen Shots Jun. 26, 2000.

VPS Impression Material, Stevenson Dental Research—Dental Times, vol. 2, No. 1, Summer/Spring (1999), pp. 1 thru 8.

3M Imprint II Impression Material System, 3M Imprint Impression Material, 3M Dental Products Division, Building 275–2SE–03, 3M Center, St. Paul, MN 55144, http://www.mmm.com/dental (4 pages)—Screen Shots Sep. 21, 2000.

3M Impression Materials, Patterson Dental Products, "Summer Celebration," (1999), pp. 23, http://www.pattersondental.com (1 page)—Screen Shot Sep. 21, 2000.

Parkell Dental Impression Materials, 155 Schmitt Blvd., P.O. Box 376, Farmington, New York 11735, http://www.parkell.com/blumousse.asp (2 pages)—Screen Shots Sep. 21, 2000.

Sofreliner MS, Tokuyama Amerca, 1875 South Grant Street, Suite 570, San Mateo, CA 94402 http://www.tokuyamaamerica.com/Sofreliner.htm (3 pages)—Screen Shots Jun. 14, 2000.

Sultan Three Way Impression Materials, Sultan Dental Products, 242 S. Dean Street, Englewood, NJ 07631 http://www/sultandental.com (3 pages)—Screen Shots Sep. 21, 2000.

ASAP Introductory Kit, DMD Dental Medical Diagnostic Systems, Inc., 6416 Variel Avenue, Woodland Hills, CA 91367 http://www.dmdcorp.com/asapl.html (3 pages)—Screen Shots Sep. 21, 2000.

D–Rain Away Coil, Home Trends Outdoors, 1450 Lyell Avenue, Rochester, NY 14606 http://www.hometrendscatalog.com (1 page)—Screen Shot Sep. 21, 2000.

*Primary Examiner*—Kevin Shaver
*Assistant Examiner*—Melba Bumgarner
(74) *Attorney, Agent, or Firm*—John P. O'Banion

(57) ABSTRACT

An inflatable dental tray for creating a dental impression. The tray is inflated for retention of an impression material which solidifies after a dental structure has been impressed therein. The inflatable tray can be configured for various inflation methods and in various shapes to form full or partial impressions. In one aspect of the invention the tray is inflated with impression material that flows from apertures forming a buildup. Various additional inventive aspects include an exterior filled inflated tray, along with tubes which provide for proper mixing of impression material.

25 Claims, 17 Drawing Sheets

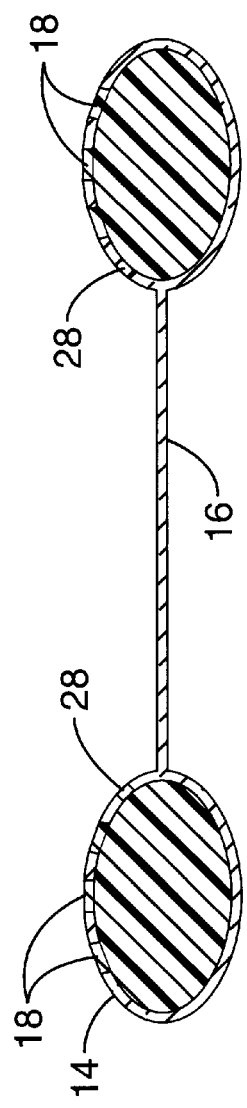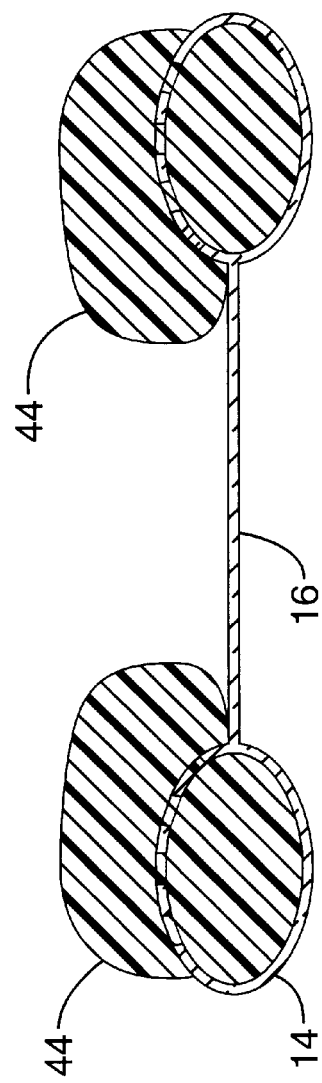

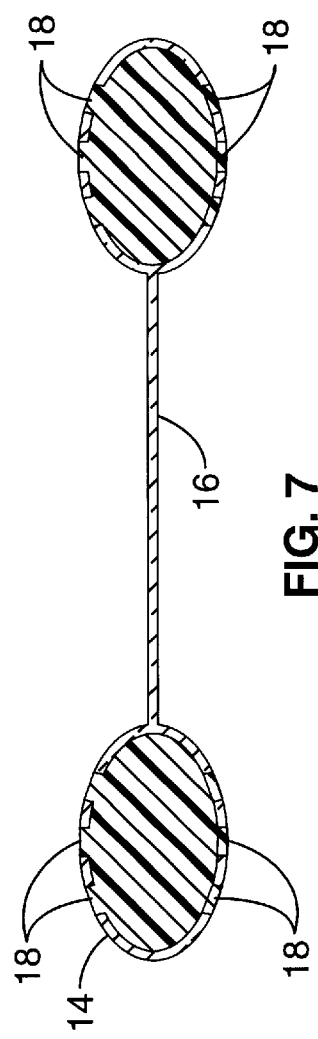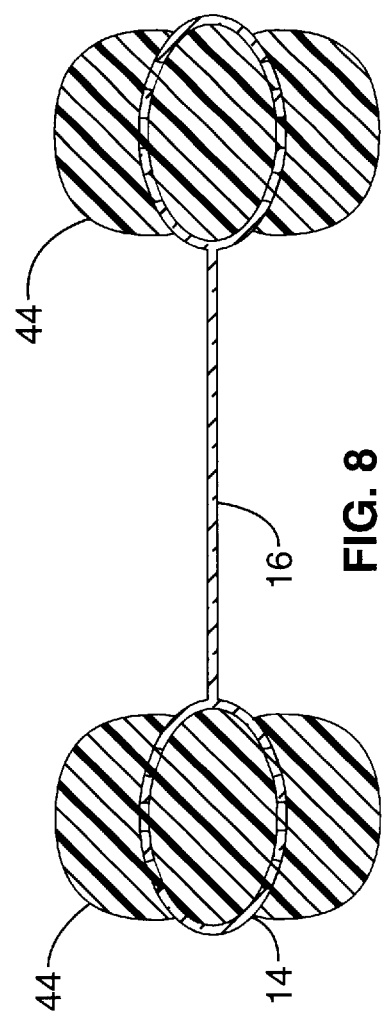

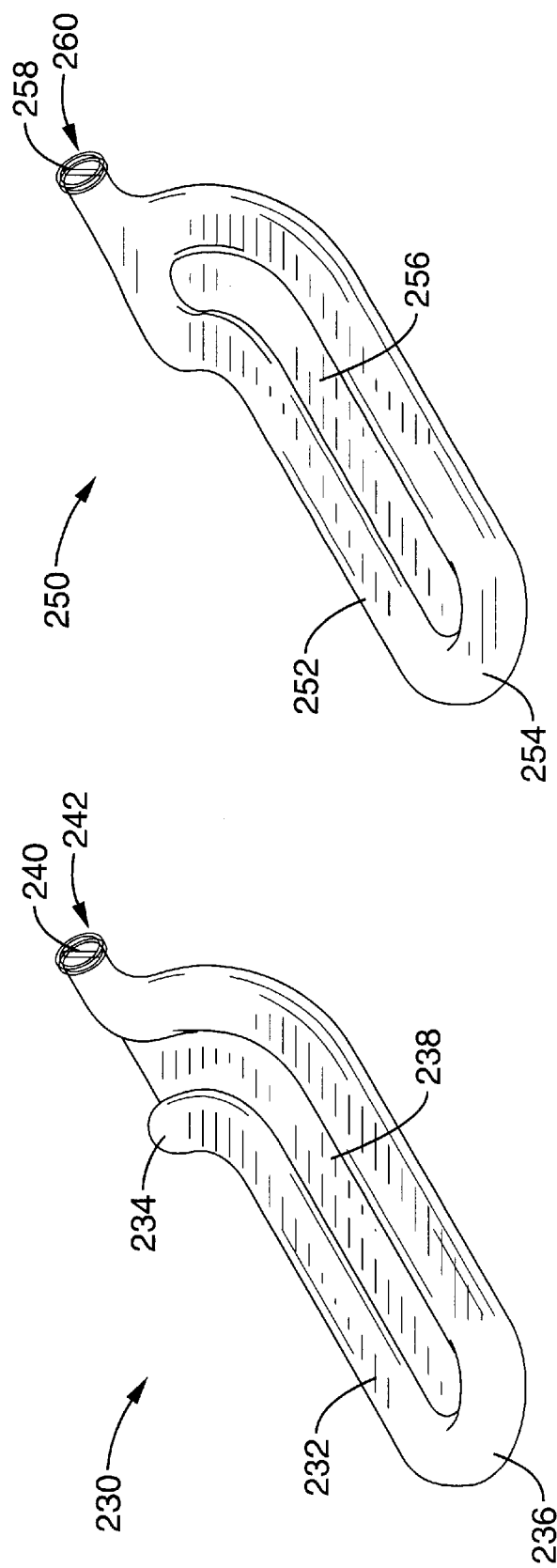

US 6,758,671 B2

INFLATABLE DENTAL IMPRESSION TRAY AND MIXING TIP

CROSS-REFERENCE TO RELATED APPLICATIONS

This application is a continuation of U.S. application Ser. No. 09/596,296 filed on Jun. 16, 2000, U.S. Pat. No. 6,364,661.

STATEMENT REGARDING FEDERALLY SPONSORED RESEARCH OR DEVELOPMENT

Not Applicable

REFERENCE TO A COMPUTER PROGRAM APPENDIX

Not Applicable

BACKGROUND OF THE INVENTION

1. Field of the Invention

This invention pertains generally to dental impression trays and more particularly to an inflatable dental impression tray and tips for use in mixing multi-part impression material.

2. Description of the Background Art

Numerous dental procedures require that accurate castings be made of dental surfaces, gums in the case of maxillary casts, or upon a patient presenting an edentulous situation. Traditional dental castings are made by applying one or more layers of liquid dental impression material to a retention shell called a tray. The liquid dental impression material is highly viscous and quick setting and typically applied as a gel or a mousse. The impression material generally is formed from two constituent components that react when mixed to facilitate quick setting. A dental impression tray loaded with the impression material is inserted in a patients mouth whereupon the mouth of the patient is closed upon the tray thereby holding it in that position until the impression material has sufficiently solidified, at which time the tray and dental impression are removed. Once removed from the patient's mouth, the tray with the solidified material contains an impression of the dental surfaces.

Impression trays in current use are variously fabricated with typical trays being a molded synthetic plastic or resin; while metal trays are now largely an anachronism. These impression trays are typified as large "U-shaped" devices for taking a full arch impression which spans the entire dental area of the upper or lower jaw, or partial arch trays which are used for taking impressions over a smaller dental areas, such as a quadrant which spans either a left or right half of a full arch (LR, LL, UR, UL). In either case, these shell form trays generally contain some form of inner and outer rigid or semi-rigid sidewall between which the impression material is retained. The trays generally are constructed of sufficient size so that the positioning of the sidewalls accommodates a variety of bite pattern shapes. Due largely to this one size fits all approach, the trays typically require a large amount of impression material for proper loading. The impression material may be made from various materials, such as alginate, polyvinylsiloxanne, polyester, wax, silicon, or a rubber compound and these materials exhibit varying levels of viscosity.

Alternatively, a few tray manufacturers have provided anatomical sets of reusable bite trays having a variety of wall heights and spacing, so that a smaller tray may be chosen whose sidewall positions more accurately reflect the size, shape, and bite pattern of the patient. Yet, in either case, the sidewalls which retain the impression material within the tray can interfere with tissue/bony interfaces, or anomalies, which prevent proper insertion as they often do not properly match the shape of the patients mouth. Current dental techniques and devices uniformly teach the use of these shell-like trays into which a two-part impression material is applied before making the dental impression. Various dual-chamber syringes and tubes are used for the dispensing and mixing of the two parts of the impression material. In addition cybernetic mixing units such as Penta™ by ESPE Mix and Mixstar™ by DMG. The dental practitioner is required to rapidly load the area within the tray with unsolidified impression material, filling it between the inner and outer impression material retention sidewalls, before the impression material begins to solidify. The tray containing the impression material is inserted into the patients mouth, adjusted into position, and the patient is directed to bite down and hold their position, so as to get a good impression. Alternatively the operator may hold the tray in place which contains the solidifying impression material. Due to their size and construction, dental impression trays are expensive; therefore many impression trays are made to be reused. Unfortunately, the process of recycling a dental tray requires removal of all hardened impression material followed by sterilization, which is typically performed within an autoclave. The sterilized tray should then be protected from contamination until reuse. Disposable clam-shell trays have also been manufactured, however, their high unit cost has traditionally been a detractor. Furthermore, in utilizing either disposable or reusable trays, the dental practitioner is required to store an assortment of these trays under antiseptic conditions.

The drawbacks inherent in current tray designs have caused many in the industry to experiment with variations of these standard dental impression trays. Recently, trays have been introduced which include an injection nozzle so that an otherwise typical shell type impression tray can be filled more easily with impression material. The impression material is still retained as in a typical shell arrangement with rigid sidewalls utilized for retention of the impression material. Other tray varieties have been introduced including trays which contain a plastic or metal perimeter upon which a fabric material is suspended so that a layer of impression material may be built-up on the fabric. However, the principle drawbacks in the use of these practitioner-filled dental impression trays, with their rigid material retention sidewalls, still remains, and the practitioner is left with the choice of using expensive disposable trays, or spending a great deal of time to clean up and recycle used trays.

The task of finding a properly fitting tray with sidewalls compatible with the oral contours of the patient can be inconvenient for the dental practitioner and uncomfortable for the patient. While in addition, the large size of these generic trays requires the use of a substantial quantity of impression material. Furthermore, the practitioner must work quickly to fill all of the tray and to fit the tray properly within the patients mouth before the impression material begins to set. The impression material is formulated to generally provide enough working time to allow this process to be completed, however if filling is accomplished very quickly the patient is left gagging on a mouthful of overflowing aqueous impression material as they wait for the material to harden.

As can be seen, therefore, the development of a dental impression tray which is inexpensive, space efficient, and does not require rigid sidewalls to retain the impression material would overcome numerous drawbacks with impression trays currently in use. The inflatable impression tray in accordance with the present invention satisfies that need, as well as others, and overcomes deficiencies in previously known techniques.

BRIEF SUMMARY OF THE INVENTION

The present invention is a dental impression tray which is inflated to achieve a desired level of rigidity and loaded with an unsolidified impression material into which dental structures are temporarily interposed during solidification. In one aspect of the invention, an inflatable impression tray containing flow apertures is filled with impression material which inflates the tray and flows out to build up on the surface into which dental surfaces may be interposed. Additional aspects provide for inflatable impression trays to which impression material is topically applied, self-inflating impression trays containing chemical reactants, and an impression material mixing tip for inflatable dental impression trays. Furthermore, in comparison with previous trays, the inflatable tray is substantially non-rigid until inflated with the impression material and does not contain the free-standing sidewalls of conventional shell-type trays.

An object of the invention is to provide an inexpensive method of making dental impressions.

Another object of the invention is to provide a disposable impression tray.

Another object of the invention is to provide a dental tray capable of being fit to a wide range of patients without sidewall interaction between the tray and the mouth of the patient.

Another object of the invention is to provide a system of making dental impressions that requires less impression material to be used per dental impression.

Another object of the invention is to provide a system of making dental impressions that eliminates the manual loading of the impression tray with impression material.

Another object of the invention is to provide a system of making dental impressions wherein the impression material is mixed as it enters the tray.

Another object of the invention is to provide a dental impression system in which the trays take up less space while being stored.

Another object of the invention is to provide an inflatable dental impression tray that is capable of being inflated with a liquid, or a gas, such as: impression material, air, water, or gas from a chemical reaction.

Another object of the invention is to provide a printable dental tray to facilitate identification and private labeling.

Another object of the invention is to provide a pleasant tasting and/or smelling dental tray for the recipient patient.

Another object of the invention is to provide impression trays in clear or colors to improve arch or quadrant identification, while preferable providing a location and mechanism by which the patients name may be adhered to the tray.

Another object of the invention is to provide a dental impression tray which is bondable by either mechanical or chemical adhesion to all dental impression materials.

Another object of the invention is to provide a tray capable of providing 3 to 50 microns of accuracy.

Another object of the invention is to provide a system of making dental impressions wherein due to the increased speed of material application, a quicker setting material formulation may be utilized to increase patient comfort and decrease the overall time required for the dental procedure.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 5 is a cross-section view of an inflatable dental tray of FIG. 1, having vertical and angled flow-apertures shown becoming fully inflated.

FIG. 6 is a cross-section view of the inflatable dental tray of FIG. 5, shown with the impression material flowing from the apertures.

FIG. 7 is a cross-section view of an inflatable dental tray having both upward and downward flow-apertures shown becoming fully inflated.

FIG. 8 is a cross-section view of the inflatable dental tray of FIG. 7, shown with the impression material beginning to flow upward and downward from apertures to form built-up impression areas.

FIG. 18 is a perspective view of an embodiment of an inflatable dental tray quadrant having a hook-shaped inflating tube wherein the unsolidified impression material is topically applied to a retained membrane.

FIG. 19 is a perspective view of an embodiment of an inflatable dental tray quadrant having an inflating tube which circumscribes a loop wherein the unsolidified impression material is topically applied to a retained membrane.

DETAILED DESCRIPTION OF THE INVENTION

Referring more specifically to the drawings, for illustrative purposes the present invention is embodied in the apparatus generally shown in FIG. 1 through FIG. 22. It will be appreciated that the apparatus may vary as to configuration and as to details of the parts, and that the method may vary as to the specific steps and sequence, without departing from the basic concepts as disclosed herein.

Figure 1:
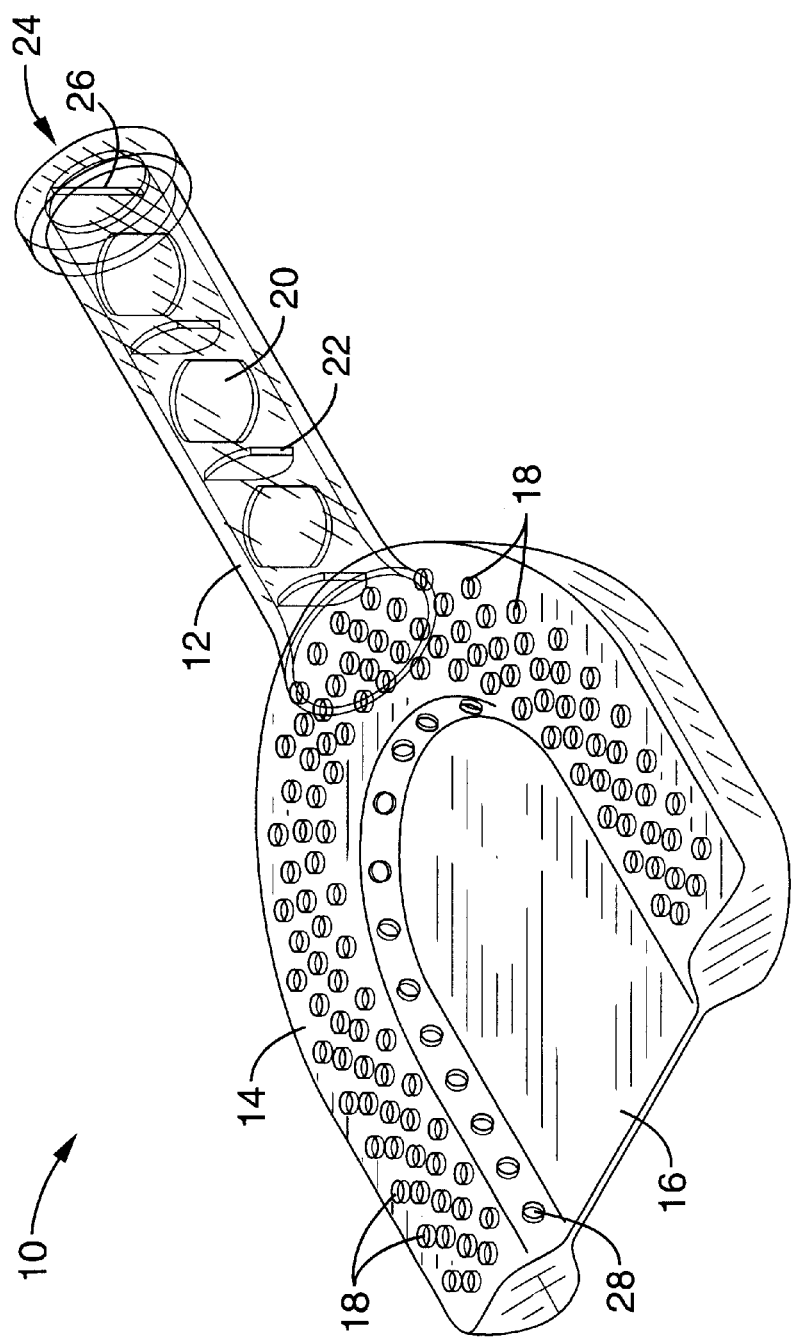
FIG. 1 is a perspective view of the inflatable dental tray according to the present invention which has flow apertures for the impression material and a fill tube.

FIG. 1 an embodiment of an inflatable dental tray 10 is shown having a rigid fill tube 12, also referred to as a mixing tip, attached to a U-shaped impression area 14 which is spanned by a membrane 16. The inflatable tray is shown configured for taking a full arch impression, preferably an upper. It will be appreciated that inflatable trays according to the invention may be manufactured in various shapes and sizes for taking impressions of selected dental regions. Circular apertures 18 are shown distributed on the top of the impression area 14. These apertures allow impression material to exude from the tray as it fills so that a material build-up region can be formed above the surface of the tray for making deep impressions. Impression material entering the inflatable impression area 14 passes through fill tube 12, or mixing tip, containing mixing baffles 20, 22, that thoroughly mix the two components of the impression material before it enters the U-shaped impression area 14 of the tray. The baffles may be oriented at opposing angles as are 20, 22 so that efficient mixing takes place. The constituent components of the impression material may enter the fill tube as separate joined streams, or lamina, of moving material which need to be properly mixed so that the proper reaction and subsequent solidification of the material will occur. The baffles operate to disrupt laminar flow through the baffles such that the lamina are folded and mixed with one another into a homogeneous stream of mixed material. The fill tube 12 receives the impression material through an injection opening 24 within which a check valve 26 is preferably located to prevent the impression material from leaking out of the fill tube once the fill source has been disconnected. A plurality of optional apertures 28 are located toward the inner portion of the impression tray and angled such that impression material can be directed over the membrane 16. It should be recognized that the inflatable tray of the invention is substantially non-rigid, or flaccid, prior to being inflated with impression material, more specifically, it does not require the inner and outer sidewalls for retaining a pool of impression material.

Figure 2:
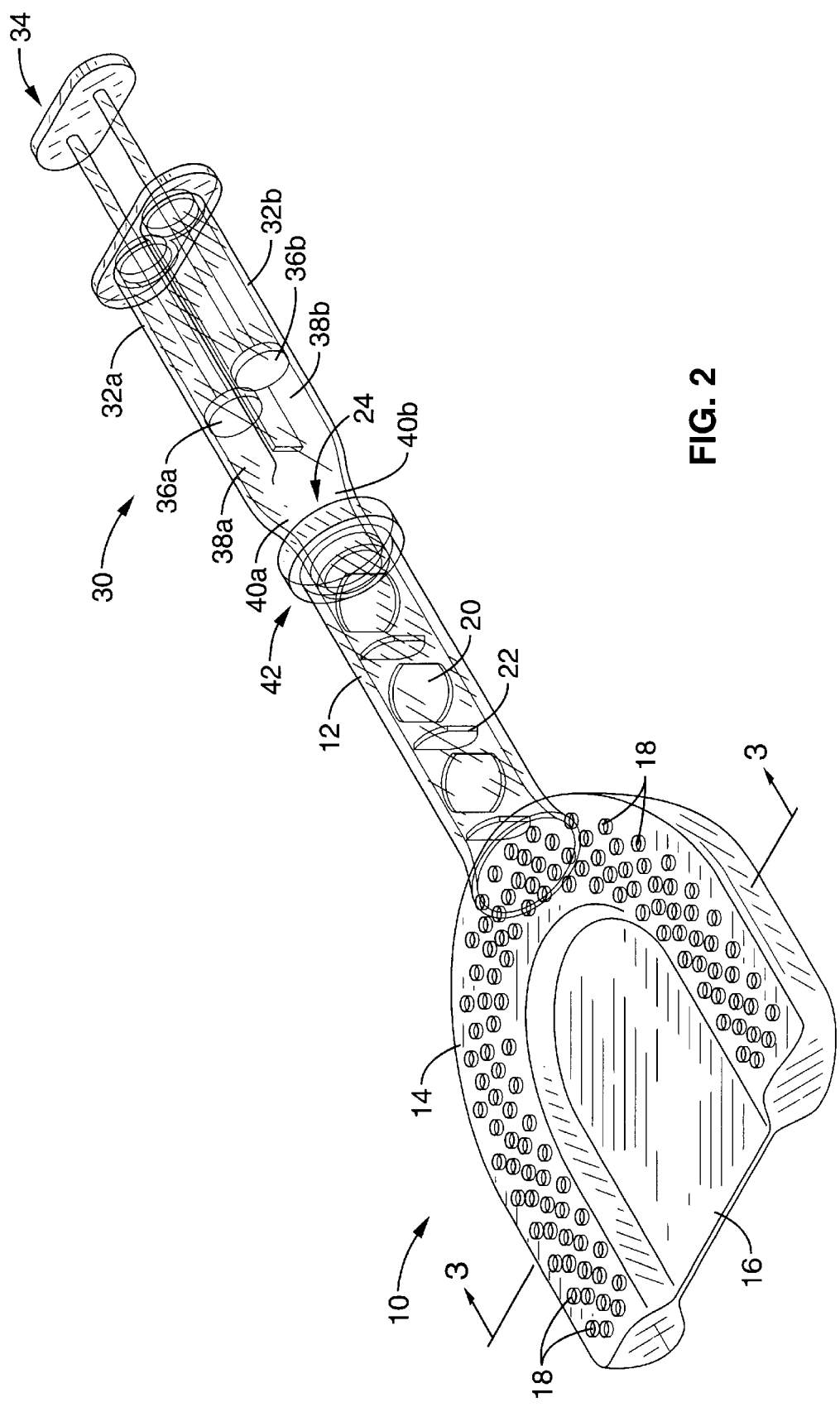
FIG. 2 is a perspective view of the inflatable dental tray of FIG. 1, shown being filled with impression material from a dual-piston syringe assembly.

FIG. 2 shows the inflatable tray 10 of FIG. 1 being filled by a dual-piston syringe 30 containing a two-part impression material through an injection opening 24 of the feed tube 12 containing baffles 20, 22 toward the flow apertures 18 within the impression area 14. The tray shown is a slight variant of that shown in FIG. 1, in that the impression tray does not contain the optional apertures 28 of FIG. 1 encircling the membrane 16. Referring to FIG. 2, the twin-tube syringe is shown by way of example, and it should be appreciated that numerous impression material sources are available, such as pistol-grip syringes. Each syringe barrel 32a, 32b contains a constituent component of the impression material, that when mixed quickly solidifies. Upon the application of pressure, the dual-plunger head 34 moves the pistons 36a, 36b to displace the two materials 38a, 38b through the necked down portions of the syringe 40a, 40b and the connector 42 which is attached to the injection opening 24 in the feed tube 12. Preferably the components of the impression material are not allowed to mix while within the body of the syringe and furthermore are prevented from mixing immediately upon entering the fill tube 12, so as to reduce clogging problems that can occur when mixed material remains within the tip of the syringe and hardens.

Figure 3:
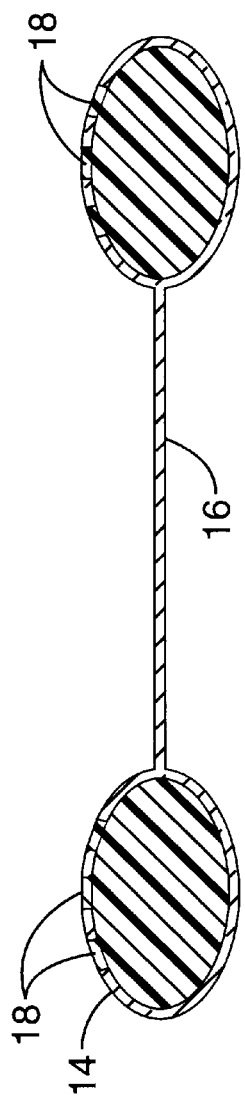
FIG. 3 is a cross-section view of an inflatable dental tray of FIG. 2, having vertical flow-apertures shown becoming fully inflated.
Figure 4:
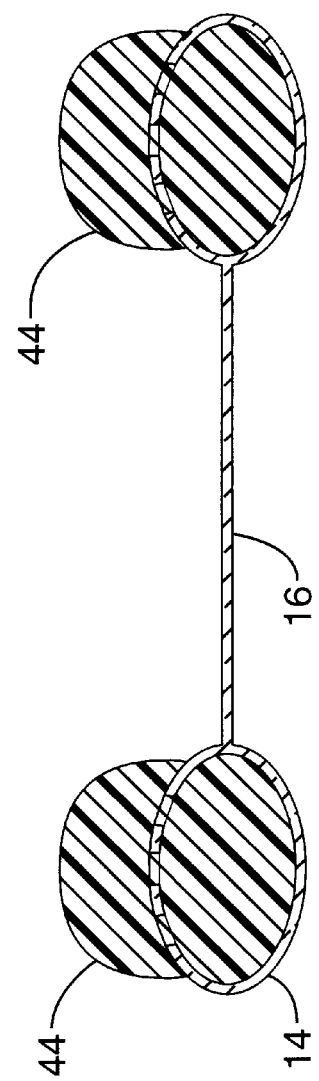
FIG. 4 is a cross-section view of the inflatable dental tray of FIG. 3, shown with the impression material beginning to flow from the apertures.

FIG. 3 shows a cross-section of the impression area 14 of a tray that has been inflated. The membrane 16 is shown attached between the inflated sides of the U-shaped impression area 14 which is configured with apertures 18. The membrane 16 preferably comprises material of the inflatable tray, and provides limited positional support to the perimeter of the inflatable tray, while it allows material to be built up for taking an impression which includes the roof of the patients mouth. The membrane 16 can be provided in various sizes, shapes, and materials. In FIG. 3, the inflatable tray of FIG. 2 is shown during the inflation process prior to the exuding of impression material from the apertures 18. FIG. 4 depicts the inflatable tray of FIG. 2 that has been inflated and further filled so as to create a build-up 44 on the portion of the inflatable tray configured with the flow apertures 18. In FIG. 5, the inflatable tray of FIG. 1, having the additional inward facing apertures 28, is shown during the inflation process prior to the exuding of impression material from the apertures 18, 28. FIG. 6 depicts the inflatable tray of FIG. 5 that has been inflated and further filled so as to create a build-up 44 on the portion of the impression area 14 of the inflatable tray configured with the flow apertures 18, 28 and extending over a portion of the membrane 16. In FIG. 7, an inflatable tray similar to FIG. 2 is shown which has apertures 18 located on both the upper and lower surfaces of the impression area 14 separated by membrane 16. The tray is shown during the inflation process prior to the exuding of impression material from the apertures 18. FIG. 8 depicts the inflatable tray having been inflated and further filled so as to create a build-up 44 both above and below a portion of the inflatable tray which is configured with the flow apertures 18. It will be appreciated that the above descriptions of flow aperture use is provided by way of example, and that a wide latitude of aperture positioning, sizing, and orientation is anticipated so as to satisfy a variety of impression requirements.

Figure 9:
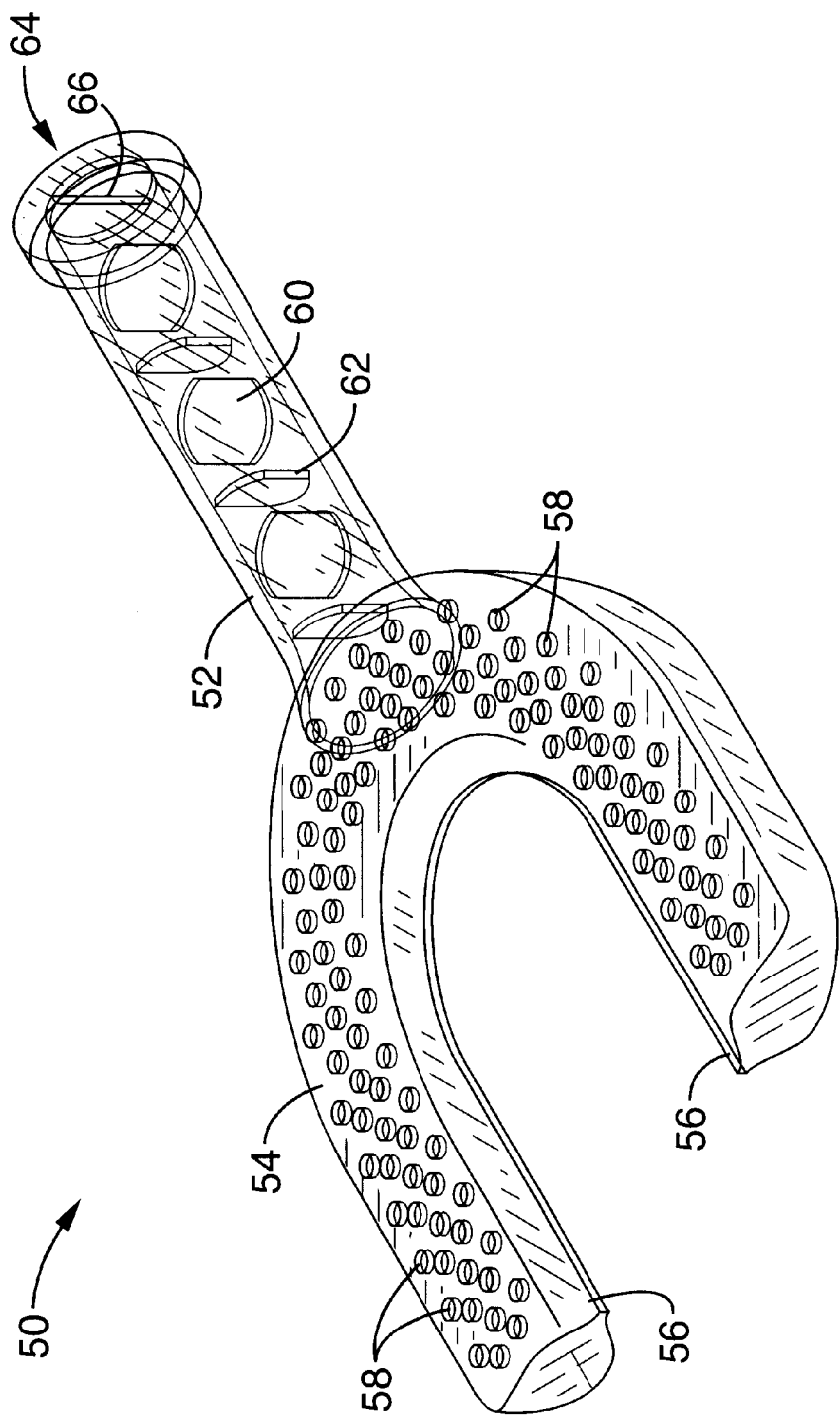
FIG. 9 is a perspective view of an inflatable dental tray according to the present invention shown configured for taking an impression of a patients lower teeth.

FIG. 9 depicts an impression tray 50 similar to that of FIG. 1, which is preferably utilized for taking lower full arch impressions of the lower dental surfaces of a patient as it is adapted to provide additional space for the tongue of the patient. The tray comprises a fill-tube 52 leading to an impression area 54 with small interior seams 56. Apertures 58 receive impression material by way of the mixing baffles 60, 62 from the injection opening 64 within which a check valve 66 is located. Use of the inflatable dental tray 50 according to the aforesaid embodiment of the present invention involves filling the tray through the fill tube until the desired amount of impression material is built up above the flow apertures, placing the tray within the mouth of a patient, and having the patient apply biting pressure until the dental surfaces are properly embedded within the impression material. After a few minutes have elapsed, the impression material solidifies and the inflatable tray with the dental impressions may be removed from the mouth of the patient. An inflatable tray according to the invention may also be filled in-situ, (while in the patients mouth) however, this may be a less preferred use as the pattern of teeth bearing down over the tray and the flow apertures could disrupt the even flow of the impression material and the formation of a correct impression. Additionally, it can be more difficult to determine how much impression material to dispense into the inflatable tray when the tray is already within the patient's mouth.

Figure 10:
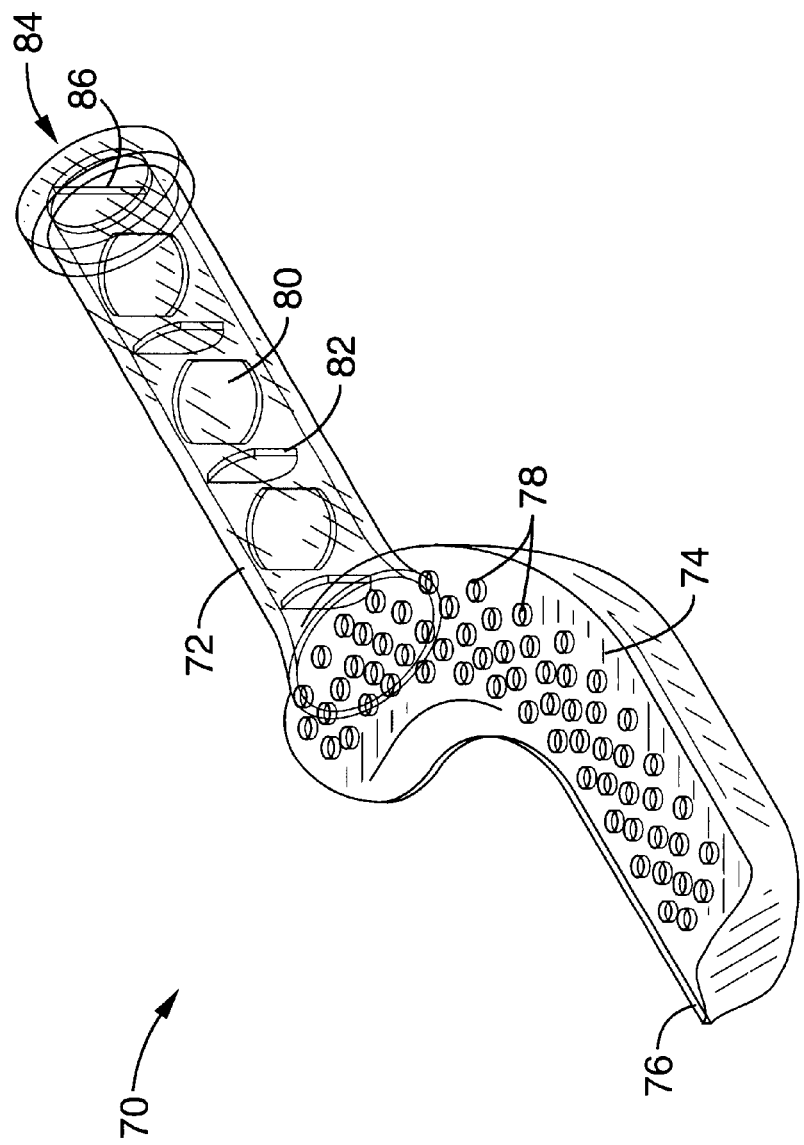
FIG. 10 is a perspective view of an inflatable dental tray quadrant according to the present invention.

FIG. 10 depicts an embodiment of a quadrant impression tray 70 which provides for taking an impression on a quarter of the dental surfaces at one time (LR, LL, UR, UL). It will be appreciated that the quadrant sized impression tray may be further reduced in size to allow the taking of an impression over smaller portions of a dental surface. The tray 70 comprises a fill-tube 72 leading to a curved impression area 74 shown here with a small interior seam 76. Apertures 78 receive impression material by way of the mixing baffles 80, 82 from the injection opening 84 within which a check valve 86 is located. It will be appreciated that the impression tray may be formed without exposed seams, such as seam 76, which is being illustrated to clarify a simple method of construction.

Figure 11:
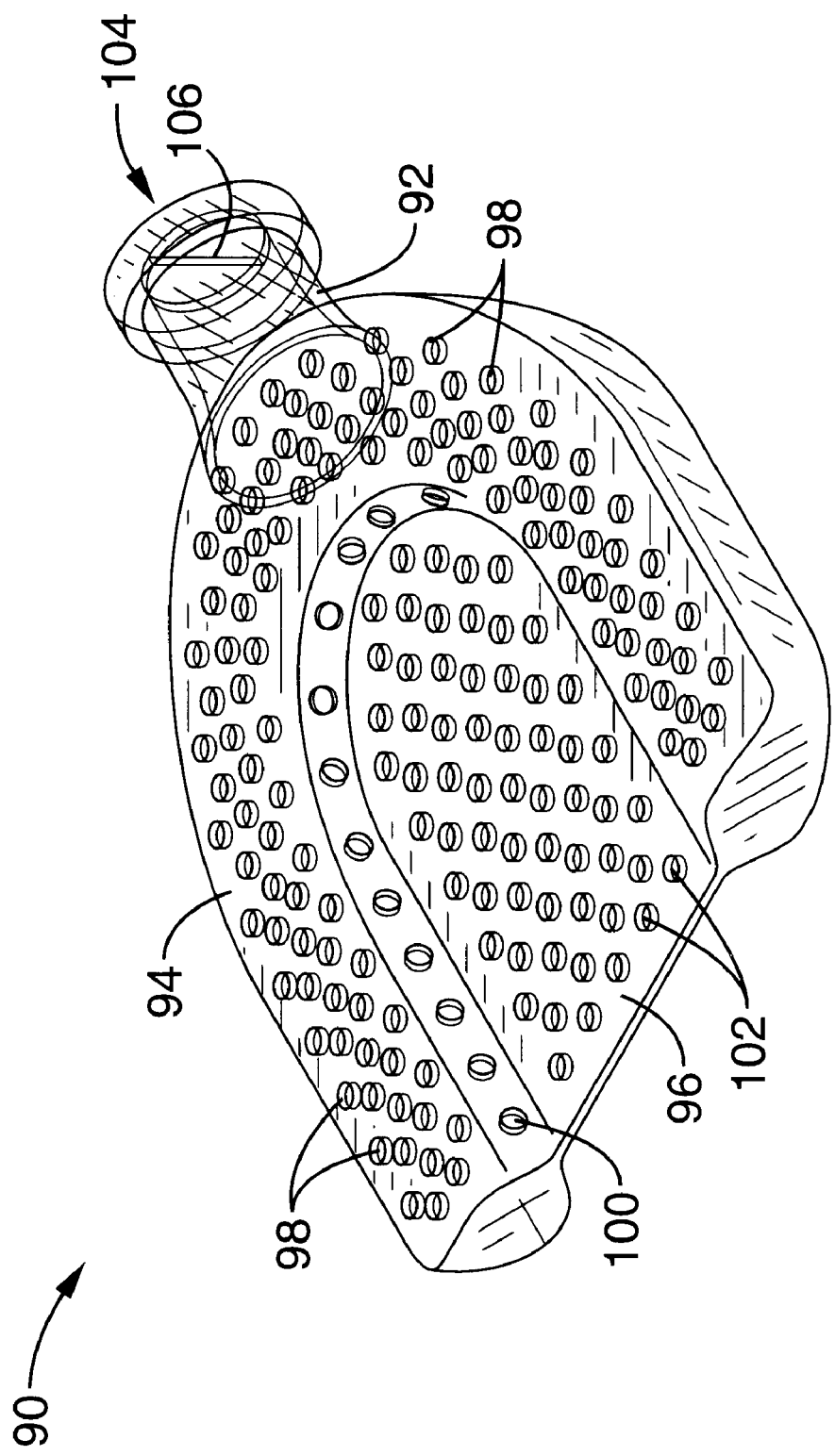
FIG. 11 is a perspective view of the inflatable dental tray according to the present invention which is configured without the attached fill tube of FIG. 1.
Figure 12:
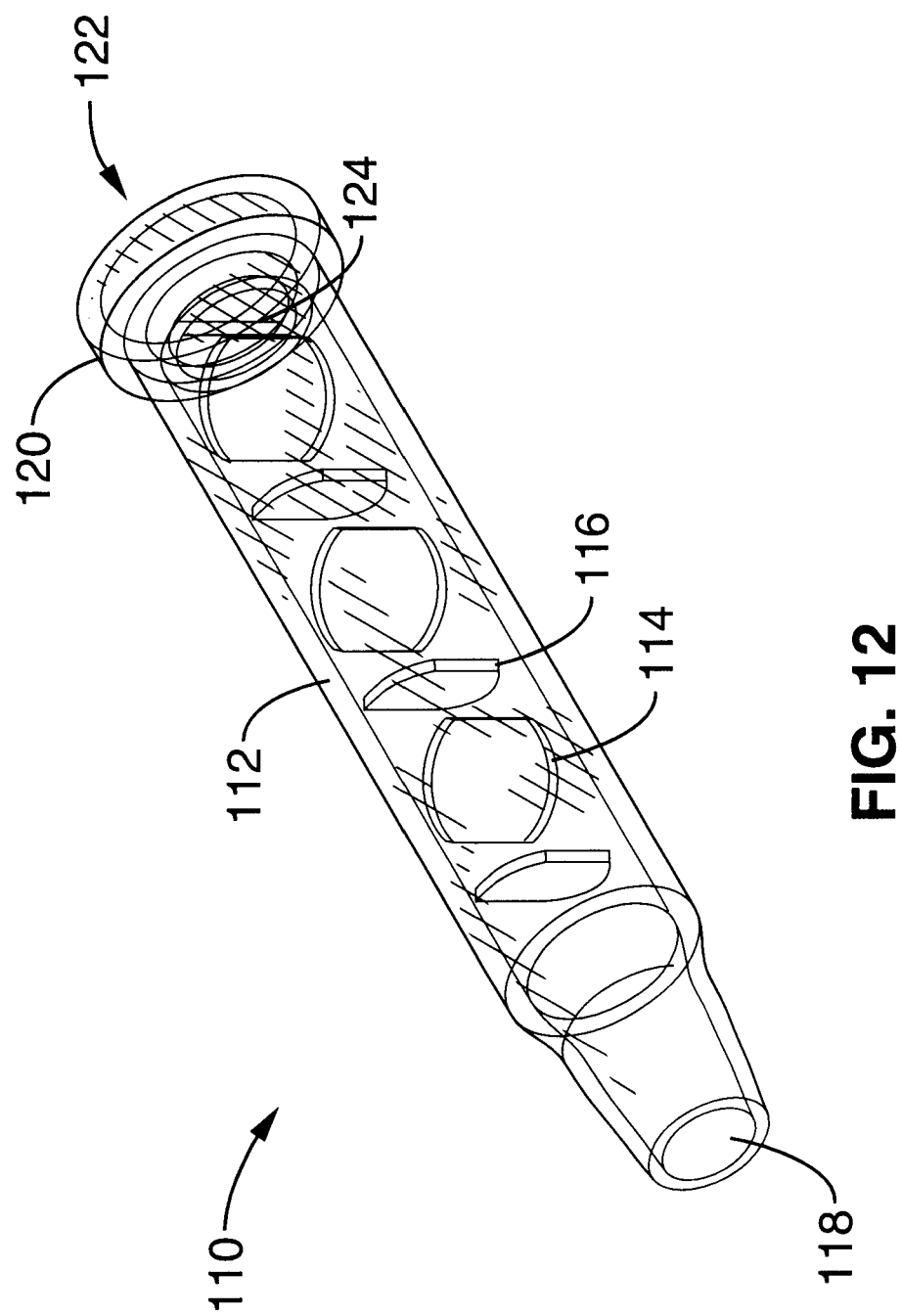
FIG. 12 is a perspective view of a mixing tip according to the present invention that provides mixing of impression material for filling the inflatable dental tray of FIG. 11.
Figure 13:
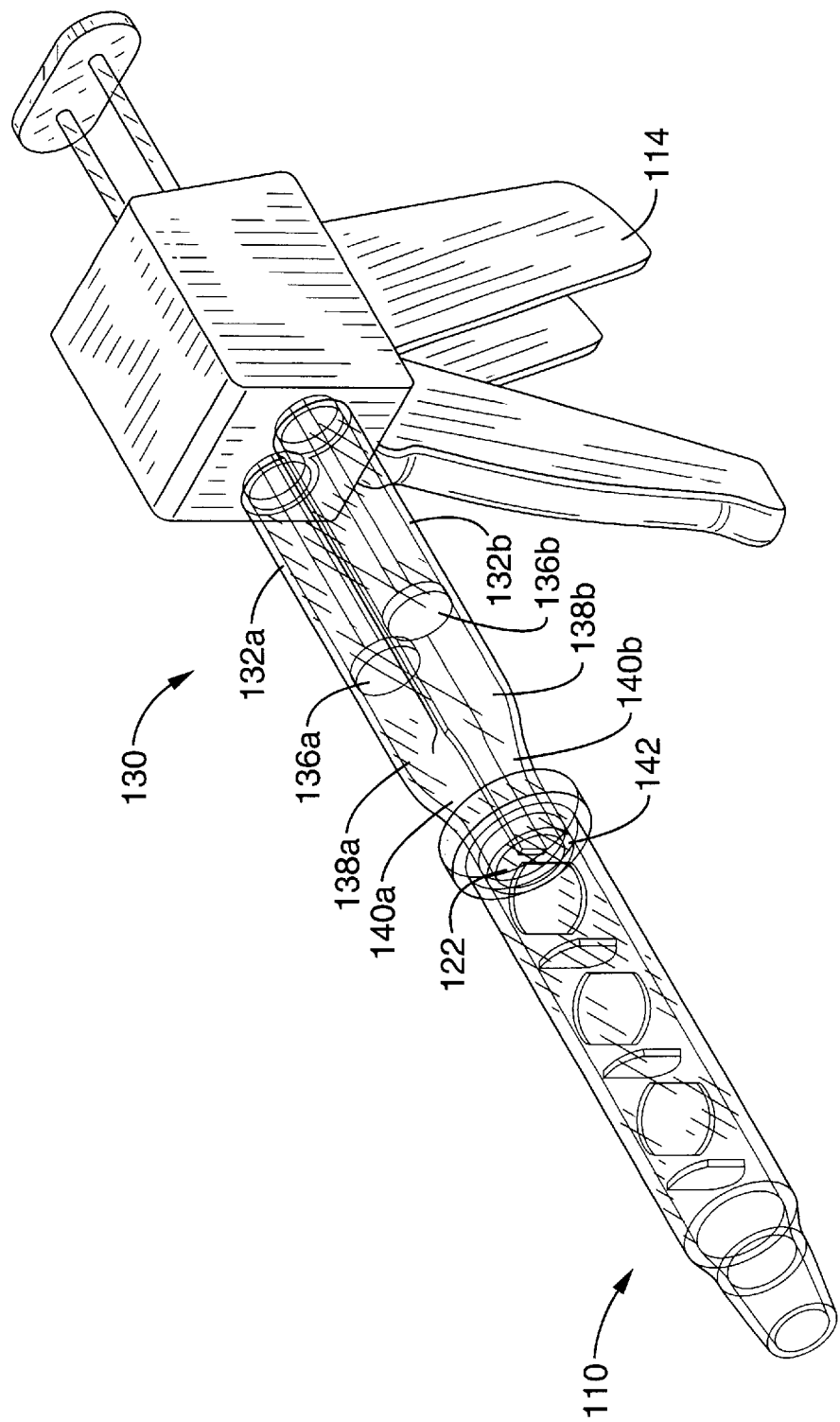
FIG. 13 is a perspective view of the mixing tip of FIG. 12 connected to a squeeze-handle dispenser for the impression material.

FIG. 11 illustrates an impression tray 90 that does not have a fill tube containing mixing baffles and, therefore, must be filled with fully-mixed impression material. The tray comprises a fill-connection 92 leading to a U-shaped impression area 94 spanned by a membrane 96. Flow apertures 98, 100 provide for distribution of impression material both above the impression area 94 and over the membrane 96 which contains impression retention apertures 102. The fill-connection 92 is shown having a fill opening 104 with a check valve 106. It will be appreciated that a variety of designs exist for constructing anti-backflow valves whereas the check valve 106 is shown by way of example. FIG. 12 is a mixing tip 110 which mixes impression material while it is conveyed from a source to an impression tray. The mixing tip 110 has an outer housing 112 in which internal baffles 114, 116, provide for the mixing of the impression material as it traverses the length of the mixing tip 110 toward a nozzle 118 which is configured for coupling with the fill opening of an inflatable dental tray. The mixing tip 110 receives impression material within an input end 120 having an opening 122 that preferably contains a check valve 124. The baffles 114, 116 within the mixing tip 110 induce a non-laminar movement, or flow, of the material passing through the tube so as to effectively "fold" any lamina within the material into one another. It will be understood that various baffling arrangements may be utilized with similar results. FIG. 13 illustrates the use of mixing tip 110 in connection with a source of impression material 130, exemplified as a pistol-grip dual-piston syringe, which may also be referred to as a "cartridge gun".

The pistol-grip syringe 130 is shown having syringe barrels 132a, 132b which each contain a constituent component of the impression material that when mixed quickly solidifies. When the pistol-grip handle 134 is squeezed the pistons 136a, 136b move to displace a portion of the material 138a, 138b through the necked down portions of the syringe 140a, 140b and the connector 142 which is attached to the injection opening 122 of a mixing tip 110. Use of a pistol-grip syringe provides additional leverage and flow control of impression material, although, alternative fluidic displacement devices may be utilized.

Inflatable dental impression trays according to the invention may be manufactured using a variety of materials and assembly methods which allow for the creation of an inflatable container for the impression material. In general, the inflatable tray 10 of FIG. 1 can be manufactured in a manner similar to that of a plastic bag, wherein two sheets of plastic material are thermally sealed together around their joined periphery by a thermal sealing tool. The material from which the inflatable tray is fabricated should be a flexible and tear resistant material having a thickness of from 2 to 5 mils (0.002–0.005 inches), preferably less than 2 to 3 mils. The inflatable tray may be manufactured from any of numerous alternative material films, such as polymer, polyethylene, polyolefin, polyamides, and polyesters with a preferable molecular weight between 50,000 and 100,000. The material of the inflatable tray may be enhanced by the additions of various chemical agents, such as color additives, odiferous additives, olfactory additives, and antimicrobial additives. Inflatable trays thereby can be produced in various colors, smells, and tastes, while having an increased resistance to microbial contamination. Additionally, the inflatable trays may be imprinted with color coding, sizing information, advertising, trade dress, or additional information such as the name of the patient. It will be appreciated that the invention can be implemented in a variety of ways without departing from the inventive principles.

Figure 14:
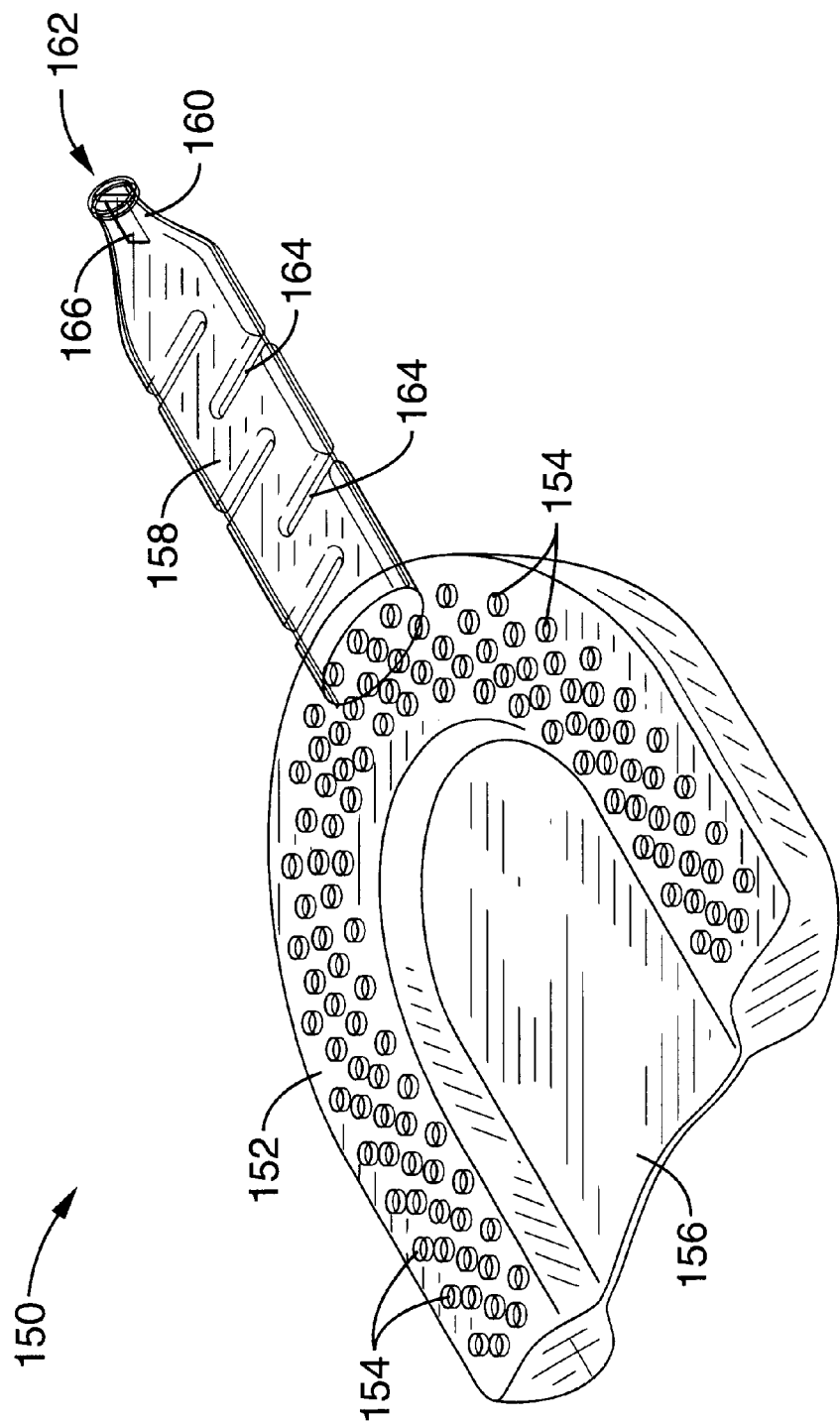
FIG. 14 is a perspective view of an embodiment of an inflatable dental tray having an inflatable fill tube with cross-wise channeling to improve mixing.
Figure 15:
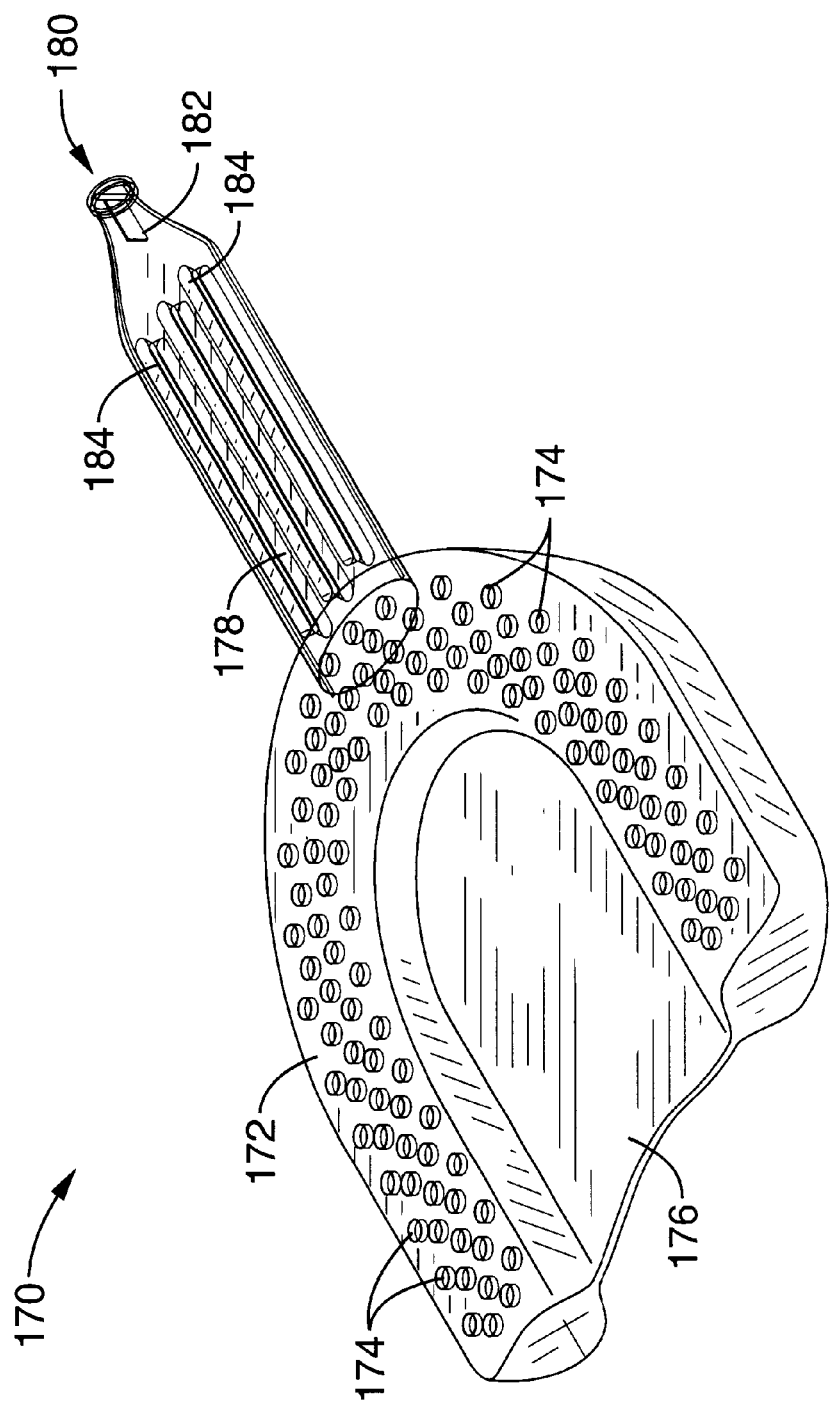
FIG. 15 is a perspective view of an embodiment of an inflatable dental tray having an inflatable fill tube with lengthwise channeling.

The inflatable tray requires a filling mechanism, or connection, so that it may be filled with the impression material. The embodiments described thus far utilize a rigid feed tube having baffles to allow filling the impression tray with fully mixed impression material. However, a variety of material filling connections may be used for this purpose, for example: a rigid tube without mixing baffles, a flexible inflatable feed tube, or a direct connection between the source of mixed impression material and the impression area of the inflatable tray without a length of feed tube. FIG. 14 illustrates an embodiment 150 of an inflatable dental tray that utilizes an inflatable fill tube. The inflatable tray has a U-shaped impression area 152 containing apertures 154 and spanned by membrane 156. Filling of the impression area 152 is accomplished by attaching an impression material source (not shown) to the inflatable fill tube 158 at the necked-down region 160 at opening 162 through which impression material is received from the impression material source to inflate and thereafter exude from the apertures 154 in the impression area 152. The inflatable fill tube may additionally contain baffles for the mixing of the material. Baffles may be exemplified as a criss-cross seam pattern 164 that provides a circuitous snaking path for the two parts of the material which disrupts laminar fluid flow (an effect of abrupt direction and aspect ratio changes) to thereby intermix the impression material as it flows through the fill tube 158. The fill tube 158 may additionally contain a fluid divider 166 that prevents mixing of constituent parts of the impression material near the fluid coupling with the source of the impression material so as to reduce the chances of residual amounts of mixed material hardening within the tip of the impression material source. FIG. 15 is an alternative embodiment 170 of an impression tray having an inflatable fill tube with longitudinal baffles. A U-shaped impression area 172 is shown having apertures 174 and being spanned by a membrane 176. The impression area receives impression material through a fill tube 178 from an opening 180. The components of the impression material are initially retained in separation by divider 182 and then caused to mix with one another within the channels formed by separations 184. It will be appreciated that an inflatable fill tube may be configured with various alternative baffle arrangements without departing from the inventive teachings.

Figure 16:
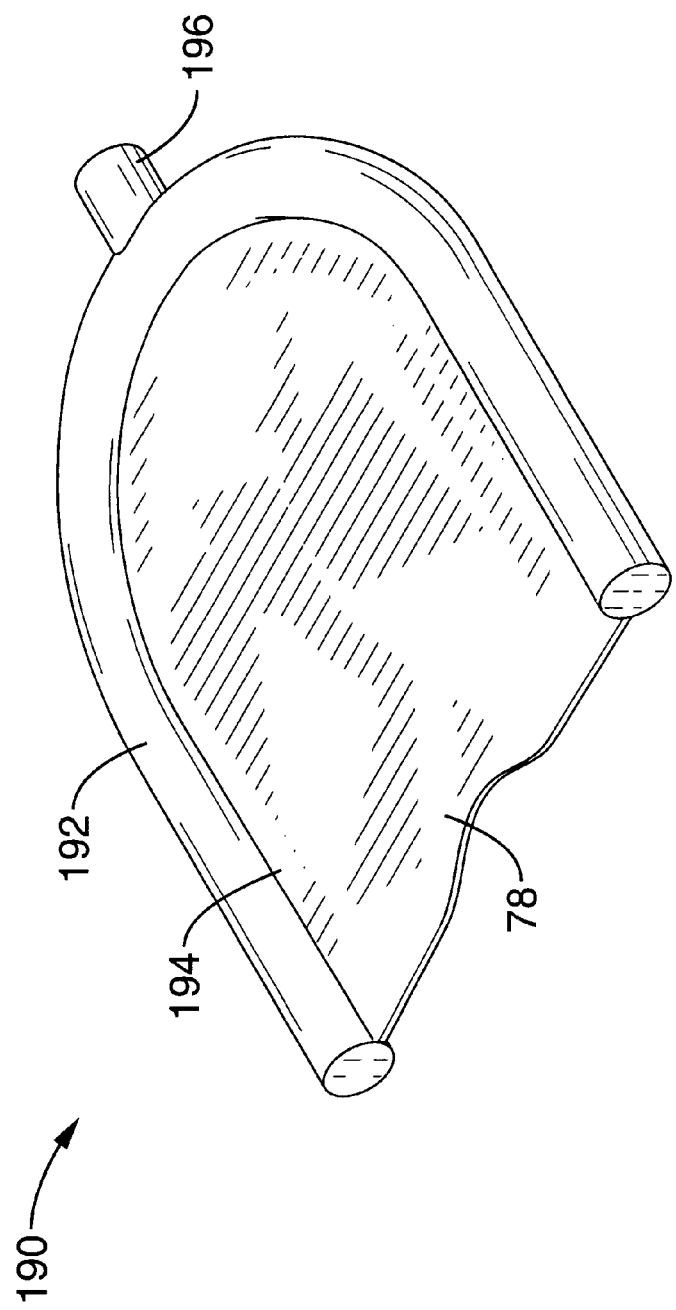
FIG. 16 is a perspective view of an embodiment of a single-rail inflatable upper dental tray wherein the unsolidified impression material is topically applied.
Figure 17:
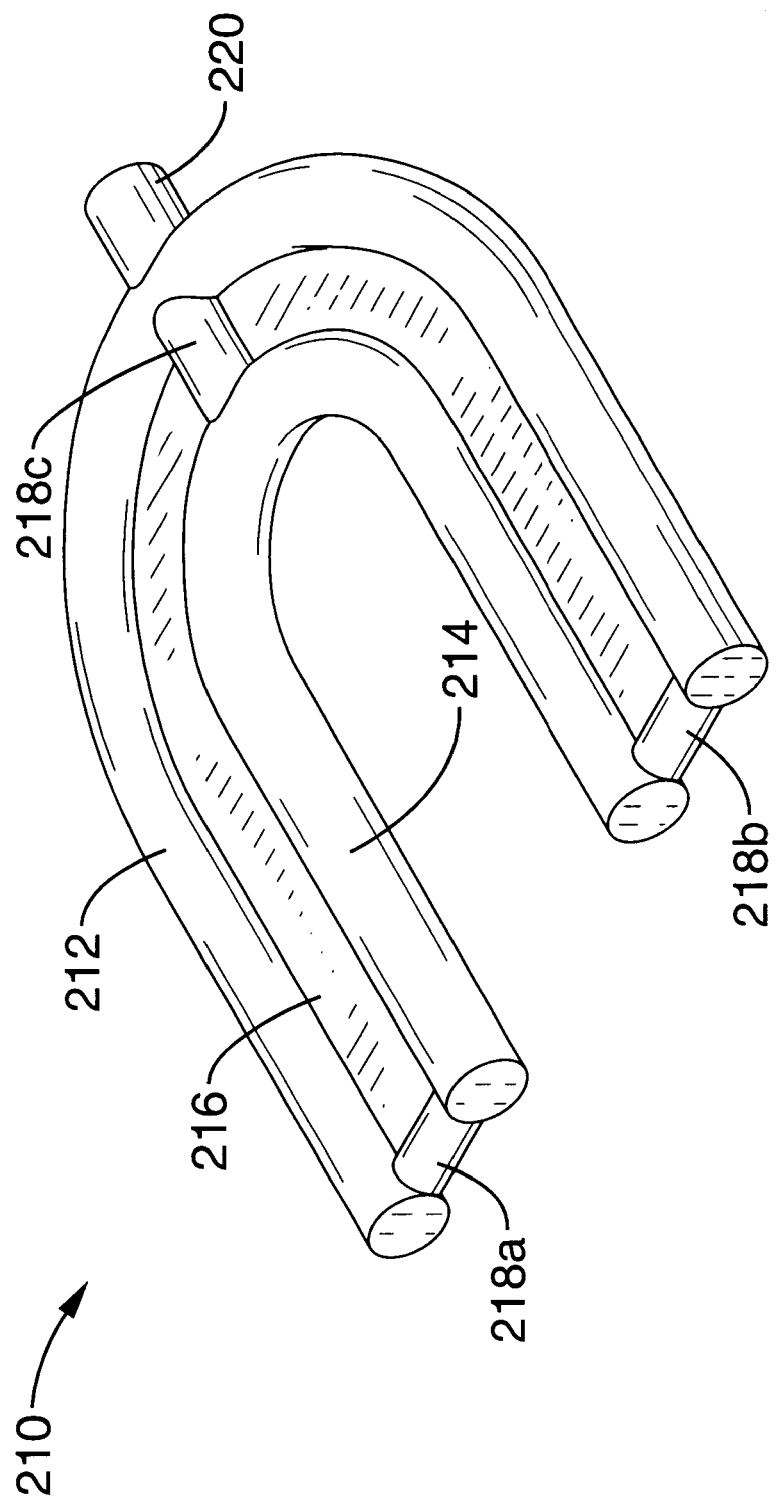
FIG. 17 is a perspective view of an embodiment of an dual-rail inflatable lower dental tray wherein the unsolidified impression material is topically applied.

The impression trays described thus far have been inflated with impression material that was allowed to exit through apertures forming built up areas of impression material. It will be recognized that inflatable trays may also be separately inflated and loaded with impression material. FIG. 16 exemplifies one such embodiment of an inflatable dental tray 190 in which the impression material is applied topically, in a similar manner much like that performed with a typical shell-type tray. This tray is configured preferably for taking upper impressions since it has a membrane 194 across the full-span of the inflatable tube 192. An outer perimeter inflatable sidewall 192 is spanned by a membrane 194 and filled through an input 196 which includes a valve (not shown). The tray is filled through the valve at the input 196 with a selected gas or liquid until it becomes sufficiently rigid, whereupon the impression material is applied to one or both sides of the inflatable tray. Tray inflation may be provided by various means, including but not limited to: compressed air, gases, water, and curable materials. FIG. 17 is a U-shaped inflatable impression tray 210 similar to that of FIG. 16, however, it is configured with dual-inflation tubes 212, 214, having a membrane 216 which spans between the tubes and leaves the center portion of the tray open. The dual-inflation tubes are shown fluidly interconnected 218a, 218b, 218c wherein the fluid received at the input 220 is evenly distributed.

Figure 21:
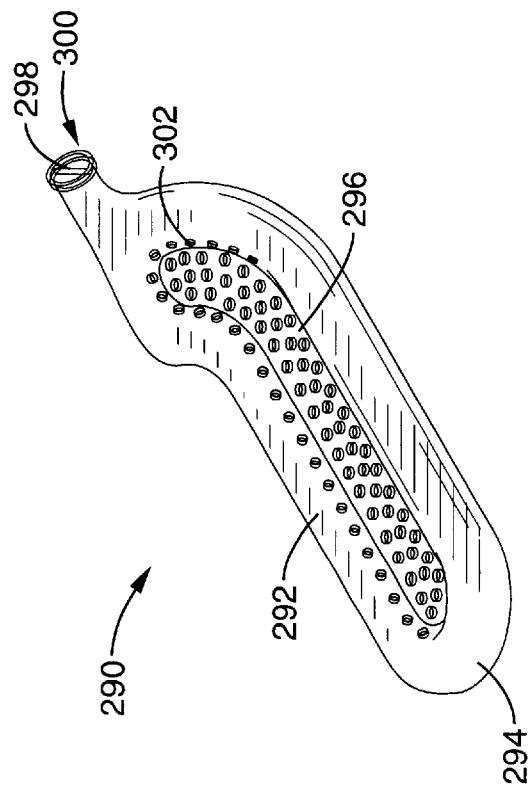
FIG. 21 is a perspective view of an embodiment of an inflatable dental tray quadrant having an inflating tube which circumscribes a loop and contains impression material flow apertures for directing material over the retained membrane.
Figure 20:
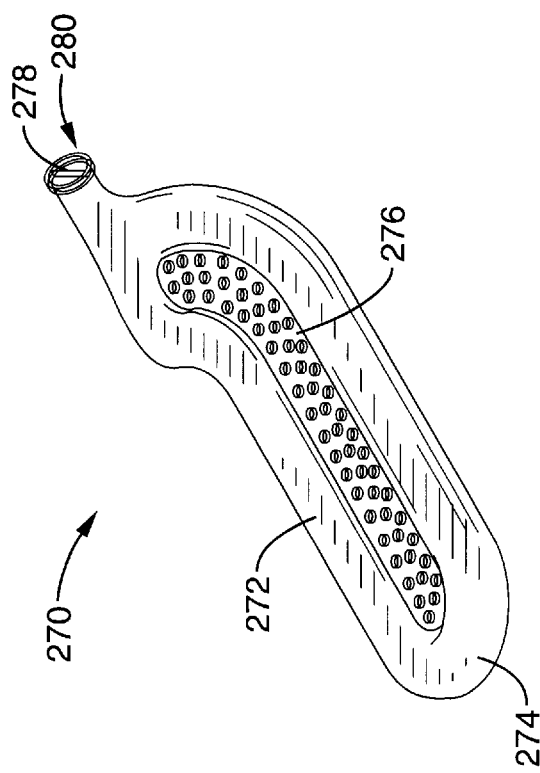
FIG. 20 is a perspective view of an embodiment of an inflatable dental tray quadrant having an inflating tube which circumscribes a loop wherein the unsolidified impression material is topically applied to a retained membrane containing apertures.

An inflatable impression tray according to the present invention may be implemented in a variety of additional shapes and styles. Another embodiment 230 of FIG. 18 illustrates a hook-shaped quadrant tray wherein an inflation tube 232 is configured in a hook shape with an end 234 and a bend 236. The area between the sides of the inflation tube are spanned by a membrane 238 upon which impression material may be topically applied. The inflation tube 232 has a filler input 240 with a valve 242 to allow for liquid or gas filling to attain sufficient structural rigidity to accept the impression material. An additional quadrant tray 250 is exemplified in FIG. 19 wherein the inflation tube 252 forms a loop with a sharp bend 254 to form a substantially narrow loop which is spanned by a membrane 256 upon which the impression material is to be topically applied. The inflation tube 252 has a filler input 258 with valve 260 providing for liquid or gas filling. FIG. 20 is another example of an impression tray 270 wherein the membrane 276 spanning the loop of the inflation tube 272 is configured with structures, herein depicted as round apertures, to increase adherance between the topically applied impression material and the impression tray. The tray is shown in a narrow quadrant configuration with bend 274, and a filler input 278 containing valve 280. A hybrid approach to a quadrant impression tray 290 is depicted in FIG. 21 wherein an inflatable tube 292 forms a narrow loop with bend 294 which is spanned by a membrane 296 having apertures therein and filled at a filler input 298 containing a valve 300. This impression tray is configured for filling with impression material and is adapted with a plurality of flow apertures 302 along the inflatable tube 292 so that once sufficient impression material is forced into the inflatable tube 292 it will begin to flow from the flow apertures 302 and build up on the membrane 296.

Figure 22:
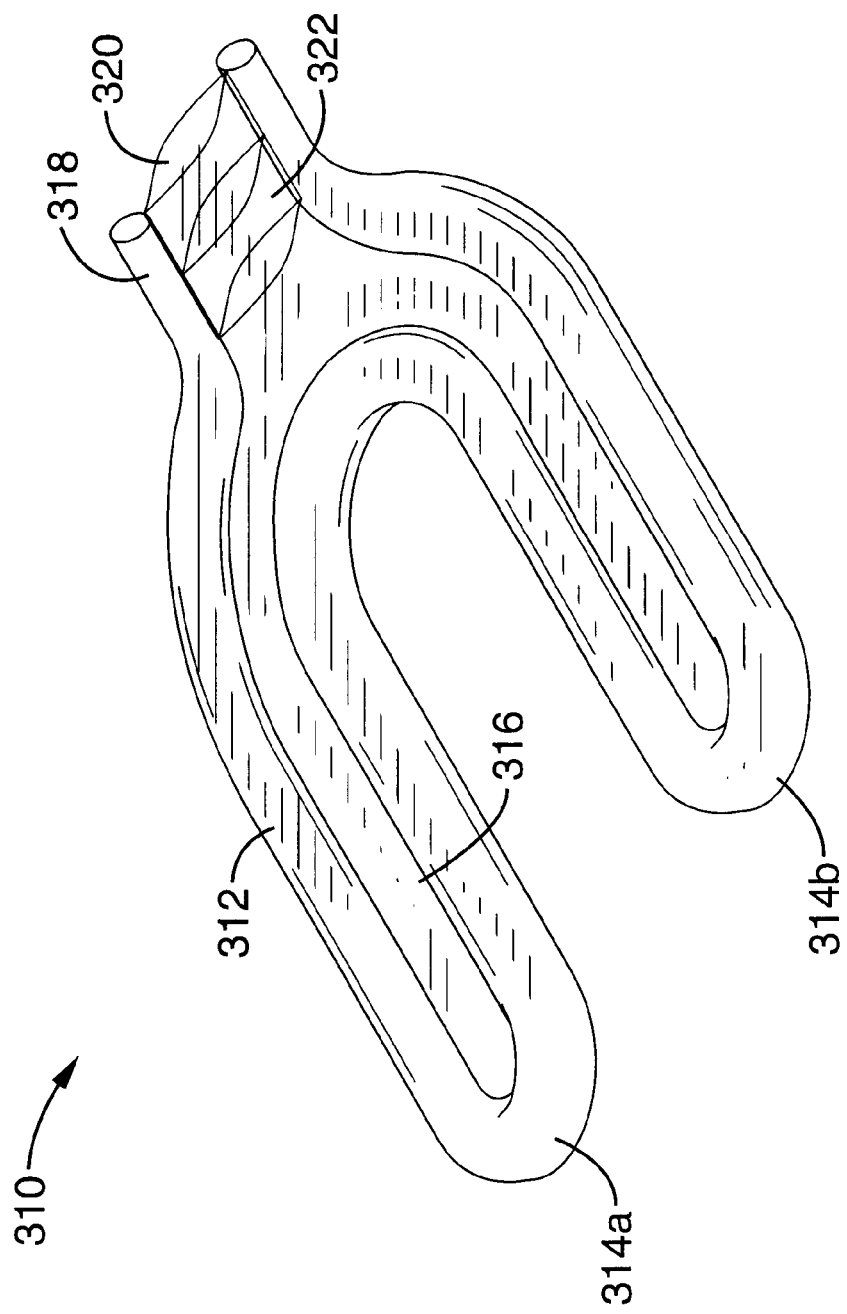
FIG. 22 is a perspective view of an embodiment of a self-filling inflatable dental tray having an inflating tube which circumscribes an inner and out perimeter wherein the unsolidified impression material is topically applied to a retained membrane.

A self-inflating impression tray may also be manufactured according to the invention wherein external sources of gas or liquid are not required to inflate the tray. FIG. 22 is an embodiment 310 of a self-inflating impression tray upon which impression material may be topically applied. An inflation tube 312 forms a U-shape with two narrow bends 314a, 314b spanned by membrane 316 to cover an upper or lower set of dental surfaces. The front 318 of the tray is configured with a pair of compartments 320, 322 containing chemical reactants that react when mixed to generate the requisite amount of gas to inflate the tube at a sufficient pressure. The compartments are bounded by fixed walls 324, 326, and separated by a rupturable membrane 328, which upon rupturing opens up apertures within the walls of the tube 312 to allow filling by the generated gas. It is preferable that the reacting chemicals be non-toxic, an example of which is sodium bicarbonate and citric acid. These reactants are stored in the separate compartments and preferable brought into contact by rupturing a membrane so that the gas created thereafter inflates the tube making the tray rigid. Various additional chemical expansion mechanisms will be well known to those of ordinary skill in the art.

Accordingly, the use of an inflatable tray as taught herein provides numerous benefits for both dental practitioners and patients. The following are given as additional examples and not as limitations to the practice of the present invention. It should be recognized that the inflatable tray 10 of FIG. 1 may be configured for various shapes and sizes to create impressions of portions of the various dental surfaces, some of which have been described. An inflatable tray being filled with impression material may be constructed with apertures for allowing impression material flow out and build up on the outside, however, an inflatable tray may be constructed without the apertures, wherein as the patient bites down on a thin exterior layer so that it ruptures or stretches to conform to the dental structure to create an impression. Inflatable trays with apertures are preferred over the non-aperture trays as they benefit from having additional impression material in the buildup areas and can be filled without trapping air bubbles. Preferably, the inflatable tray and the impression material which it retains should become either mechanically or chemically attached to one another to stabilize the finished impression. Various embodiments of the inflatable trays have been exemplified for the present invention which enhance the process of making dental impressions, so that impressions can be created in less time, with more comfort, and at reduced cost.

Although the description above contains many specificities, these should not be construed as limiting the scope of the invention but as merely providing illustrations of some of the presently preferred embodiments of this invention. Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An apparatus for creating a dental impression, comprising:
    (a) an inflatable base member configured for placement adjacent to a surface in the mouth of a patient; and
    (b) means for inflating said base member until it is sufficiently rigid to retain a quantity of impression material;
    (c) wherein the base member is configured for inflation by mixing chemicals contained within the base member that react to generate a volume of gas sufficient to inflate the base member.

2. An apparatus as recited in claim 1, further comprising a plurality of apertures with said base member through which impression material can flow when injected into said base member.

3. An apparatus as recited in claim 2, further comprising a fill tube attached to said base member, said fill tube having a plurality of internal baffles configured for mixing impression material components as said components flow through said fill tube and into said base member.

4. An apparatus as recited in claim 1, wherein the base member in an uninflated state is substantially planar.

5. An inflatable dental tray for making solid impressions of dental surfaces, comprising:
    (a) an inflatable base member adapted for positioning adjacent a surface in the mouth of a patient;
    (b) means for filling said inflatable base member with a fluid, such as a liquid or gas, to inflate the base member;
    (c) wherein said means for filling the inflatable base member with a fluid comprises an opening within said inflatable base member which is configured to receive a fluid, such as a liquid or gas, to inflate the base member; and
    (d) flow apertures in said inflatable base member which allow impression material being used to inflate the base member to flow out and build up on the surface of said base member and into which dental surfaces may be interposed.

6. An inflatable dental tray for making solid impressions of dental surfaces, comprising:
    (a) an inflatable base member adapted for positioning adjacent a surface in the mouth of a patient;
    (b) means for filling said inflatable base member with a fluid, such as a liquid or gas, to inflate the base member;
    (c) wherein said means for filling the inflatable base member with a fluid comprises an opening within said inflatable base member which is configured to receive a fluid, such as a liquid or gas, to inflate the base member; and
    (d) a valve positioned within said base member to prevent fluids being received for inflation of said base member from a source of fluids from escaping through said opening upon disconnection of said source of fluids after inflation has been performed.

7. An inflatable dental tray making solid impressions of dental surfaces, comprising:
    (a) an inflatable base member adapted for positioning adjacent a surface in the mouth of a patient; and
    (b) means for filling said inflatable base member with a fluid, such as liquid or gas, to inflate the base member;
    (c) wherein the inflatable base member is constructed of an upper and lower layer of a flexible film material which is joined together to form an inflatable chamber.

8. An inflatable dental tray as recited in claim 5, 6, or 7, wherein the inflatable base member does not have free-standing retention sidewalls for retaining a quantity of impression material prior to inflation.

9. An inflatable dental tray making solid impressions of dental surfaces, comprising:
    (a) an inflatable base member adapted for positioning adjacent a surface in the mouth of a patient; and
    (b) means for filling said inflatable base member with a fluid, such as a liquid or gas, to inflate the base member;
    (c) wherein the inflatable base member does not have free-standing retention sidewalls for retaining a quantity of impression material prior to inflation.

10. An inflatable dental tray as recited in claim 5, 6, 7 or 9, wherein the means for filling the inflatable base member comprises means for bringing reactive chemicals into contact with one another that were previously contained separately, wherein the reaction of the chemicals generates a gas that inflates the inflatable base member.

11. An inflatable dental tray as recited in claim 10, wherein a pair of chemicals are retained in separate compartments within the base member and configured to be brought into contact by rupturing a separating material.

12. An inflatable dental tray as recited in claim 7 or 9, wherein the means for filling the inflatable base member with a fluid comprises an opening within said inflatable base member which is configured to receive a fluid, such as a liquid or gas, to inflate the base member.

13. An inflatable dental tray as recited in claim 5, 6, 7 or 9, further comprising flow apertures in said inflatable base member which allow impression material being used to inflate the base member to flow out and build up on the surface of said base member and into which dental surfaces may be interposed.

14. An inflatable dental tray as recited in claim 13, further comprising a fill tube attached to the opening within said inflatable base member and configured with mixing baffles capable of mixing the constituent parts of a multipart impression material flowing therein.

15. An inflatable dental tray as recited in claim 14, wherein said fill tube is inflatable and is inflated upon receipt of impression material.

16. An inflatable dental tray as recited in claim 5, 7 or 9, further comprising a valve positioned within said base member to prevent fluids being received for inflation of said base member from a source of fluids from escaping through said opening upon disconnection of said source of fluids after inflation has been performed.

17. An inflatable dental tray as recited in claim 5, 6, or 9, wherein the inflatable base member is constructed of an upper and lower layer of a flexible film material which is joined together to form an inflatable chamber.

18. An inflatable dental tray as recited in claim 5, 6, 7 or 9, wherein the inflatable base member is substantially flaccid prior to inflation.

19. An inflatable dental tray as recited in claim 5, 6, 7 or 9, further comprising additives within the material of the inflatable dental tray capable of altering material characteristics and selected from the group of characteristic properties consisting of smell, taste, color, and bacteriological prophylaxis.

20. An apparatus for use in taking dental impressions in the mouth of a patient, comprising:
   an inflatable tray configured for holding impression material when inflated;
   a fill port; and
   a fill tube connected to said fill port;
   wherein said fill tube includes a plurality of mixing baffles.

21. An apparatus for use in taking dental impressions in the mouth of a patient, comprising:
   an inflatable tray configured for holding impression material when inflated;
   a fill port; and
   a fill tube connected to said fill port;
   wherein said fill tube is inflatable.

22. An apparatus as recited in claim 20 or 21, further comprising a plurality of apertures in said base member in flow communication with said fill port.

23. An apparatus as recited in claim 20 or 21, wherein said fill port is configured to receive impression material.

24. An apparatus as recited in claim 20 or 21, wherein said base member is configured for inflation by impression material injected into said fill port.

25. An apparatus as recited in claim 20 or 21, wherein said apertures are configured for exhausting impression material injected into said base member through said fill port.

* * * * *